United States Patent [19]

Thigpen et al.

[11] Patent Number: 4,550,213

[45] Date of Patent: Oct. 29, 1985

[54] METHOD OF MANUFACTURE FOR PARAFORMALDEHYDE PRILLS

[75] Inventors: Hubert H. Thigpen, Corpus Christi, Tex.; Richard J. Clos, Vancouver, Wash.

[73] Assignee: Celanese Corporation, New York, N.Y.

[21] Appl. No.: 625,942

[22] Filed: Jun. 29, 1984

[51] Int. Cl.⁴ ............................................. C07C 47/02
[52] U.S. Cl. .................... 568/458; 568/420; 568/449; 568/457
[58] Field of Search ............ 568/493, 492, 458, 449, 568/448, 420, 421, 422, 457; 260/695

[56] References Cited

U.S. PATENT DOCUMENTS

| | | | |
|---|---|---|---|
| 2,568,018 | 9/1951 | MacLean et al. | 568/457 |
| 3,118,859 | 1/1964 | Delassus et al. | 568/457 |
| 3,300,535 | 1/1967 | Yakimik et al. | 568/457 |
| 3,316,309 | 4/1967 | Mann et al. | 568/457 |
| 3,423,363 | 1/1969 | Fournel et al. | 568/457 |
| 3,595,926 | 7/1971 | Mann et al. | 568/457 |
| 3,632,655 | 1/1972 | Paleologo et al. | 568/457 |
| 3,772,392 | 11/1973 | Paleologo et al. | 568/457 |
| 4,036,891 | 7/1977 | Moller et al. | 568/457 |

FOREIGN PATENT DOCUMENTS

| | | | |
|---|---|---|---|
| 852650 | 9/1970 | Canada | 568/449 |
| 908774 | 10/1962 | United Kingdom | 568/494 |

*Primary Examiner*—Werren B. Lone
*Attorney, Agent, or Firm*—D. R. Cassady

[57] ABSTRACT

An improvement for manufacturing paraformaldehyde prills from an aqueous solution of formaldehyde which comprises polymerizing the formaldehyde in the presence of a catalyst of sodium hydroxide in a concentration of from about 0.5 to about 5 ppm, aging the resulting mixture at about 100° to about 130° C. for about 10 to about 60 minutes, spraying the aged mixture into a prilling tower at from about 100° to about 130° C., collecting the prills in a fluidized bed at the base of the tower at from about 45° to about 60° C., removing the prills to a separate vessel where the prills further polymerize and dry at from about 15° to about 30° C. for about 3 to about 5 hours while operating the vessel in a plugged flow manner, and collecting the resulting prills.

1 Claim, 1 Drawing Figure

METHOD OF MANUFACTURE FOR PARAFORMALDEHYDE PRILLS

BACKGROUND OF THE INVENTION

The process of prilling of a normally solid material by (1) heating the material to above the melting point, (2) spraying the molten material through nozzles into a stream of a cooling fluid, (3) maintaining the resulting solid particles in a fluid bed state until the surface is no longer sticky or tacky, (4) then collecting the solid prills is well known. Prilling of an aqueous solution of paraformaldehyde containing from about 80 to about 90 weight percent formaldehyde into a countercurrent flow of inert gas has been disclosed and claimed in several prior art U.S. patents. The most pertinent of these patents are U.S. Pat. Nos. 3,316,309; 3,595,926; 3,632,655; and 4,036,891.

In these prior art patents, the inventor recognizes the need to cure the solid prills for a time sufficient to provide a dry, non-tacky surface. Thus, in U.S. Pat. No. 3,316,309, the solution of formaldehyde is sprayed into a cooling chamber while passing a current of air having the temperature between 40° and 60° C. upward through the chamber, the inventors claim a non-sticky particulate paraformaldehyde is formed. Later, in U.S. Pat. No. 3,595,926 the same inventor has indicated that while the method is satisfactory on a small scale, the product is not sufficiently free of tackiness and quickly agglomerates causing the process to come to a standstill because of complete clogging of the nozzles. Thus, in U.S. Pat. No. 3,595,926, the inventor claims the critical aspect of the new process is that the temperature of the cooling gas is preferably between −40° C. and +30° C. and the paraformaldehyde prills remain in the fluidized bed of the cooling tower until they have been cooled to a temperature below 40° C., preferably 20° to 30° C. in order to avoid stickiness. The cooled pellets are then dried in a contact dryer to a final formaldehyde content of 92 to 97%.

In U.S. Pat. No. 3,632,655, the inventor sprays a polymerization catalyst onto the surface of the prills as they are being formed in the prilling tower. The catalyst is generally an amine, to provide a dense, highly polymerized, non-tacky surface. The process then calls for curing the prills at a temperature of from about 10° to about 20° C. lower than the softening point of the product for from about 2 to about 50 minutes.

In U.S. Pat. No. 4,036,891, the inventor claims spraying the liquid paraformaldehyde into a chamber in contact with an inert gas, removing the resultant particles at between 40° and 60° C., then passing the particles through a series of at least two other vibrating fluidized beds, fluidized by an inert gas held at below the sticking point of the polymer. It is claimed by the inventor, that it is critical that the temperature of the gas in the second or greater-numbered chamber be higher than the temperature of the gas in the first drying chamber.

In all of the prior art methods, a solid, non-sticky, round particle is formed as described.

In our hands we found that, during storage, the molecular weight of the product as prepared by these methods increased precipitously. Further investigation proved that during storage of a bulk quantity of the prills, a sizable quantity of heat was generated, presumably from the continued polymerization and dehydration of the solid prills. In bags of 2000 lbs or more, temperatures of 75° to 80° C. were encountered within 5 to 8 hours of the filling time and temperatures of at least 75° were still present after 20 hours from filling time. This high temperature in the bulk bags caused the melting point of the paraformaldehyde prills to approach 170° C. within 30 hours of filling.

SUMMARY OF THE INVENTION

This invention relates to an improved method of manufacture of prills of paraformaldehyde.

It is an object of this invention to provide a convenient form of paraformaldehyde solids which are not subject to auto-catalyzed polymerization when stored in bulk lots at ambient room temperature.

It is a further object of this invention to provide a paraformaldehyde prill which has a dry, non-sticky surface, analyzes for at least 91% paraformaldehyde immediately after manufacture, and has an extended shelf life without rapid melting point and apparent molecular weight gain due to auto-catalyzed polymerization and heating.

The prills manufactured by the method of this invention typically have the following characteristics:

They are free flowing, dustless, spheres melting at about 120° C. of which more than 95% pass through a 20 mesh (U.S.) screen. The formaldehyde content immediately after prilling is above about 91%. The prills dissolve in water to form an aqueous formaldehyde solution with no residual turbidity.

More importantly, the apparent molecular weight and melting point do not raise precipitously after manufacture when the prills are held in bulk storage.

The usual and customary methods for manufacture of formaldehyde from an aqueous solution containing at least about 85% formaldehyde comprises at least the following steps: (1) polymerizing the formaldehyde in the presence of a catalyst; (2) extruding the polymerized formaldehyde through a nozzle to form droplets which fall through a countercurrent flow of a gas in a tower to further polymerize and solidify the droplets into prills; (3) collecting the solidified prills; and (4) removing the prills from the tower. By the improved method of this invention, dilute, aqueous sodium hydroxide is added to an aqueous formaldehyde solution containing at least about 85% by weight of formaldehyde to a sodium ion concentration of about 0.5 to about 5 ppm. The resulting mixture is aged by holding at from about 100° to about 120° C. for from about 10 to about 60 minutes to further polymerize the formaldehyde. The polymerized solution is then extruded into a prilling tower at from about 100° to 120° C. in a gas; collected at the base of the tower in a fluidized bed at from about 40° C. to about 60° C.; and removed into a separate quenching vessel where the prills are further polymerized and dried at from about 15° C. to about 30° C. for from about 3 to about 5 hours and removed from the quenching vessel. The quenching vessel in the present invention is operated in a plugged flow manner without significant back-mixing of the prills during drying and further curing.

DETAILED DESCRIPTION OF THE INVENTION

Figure 1:
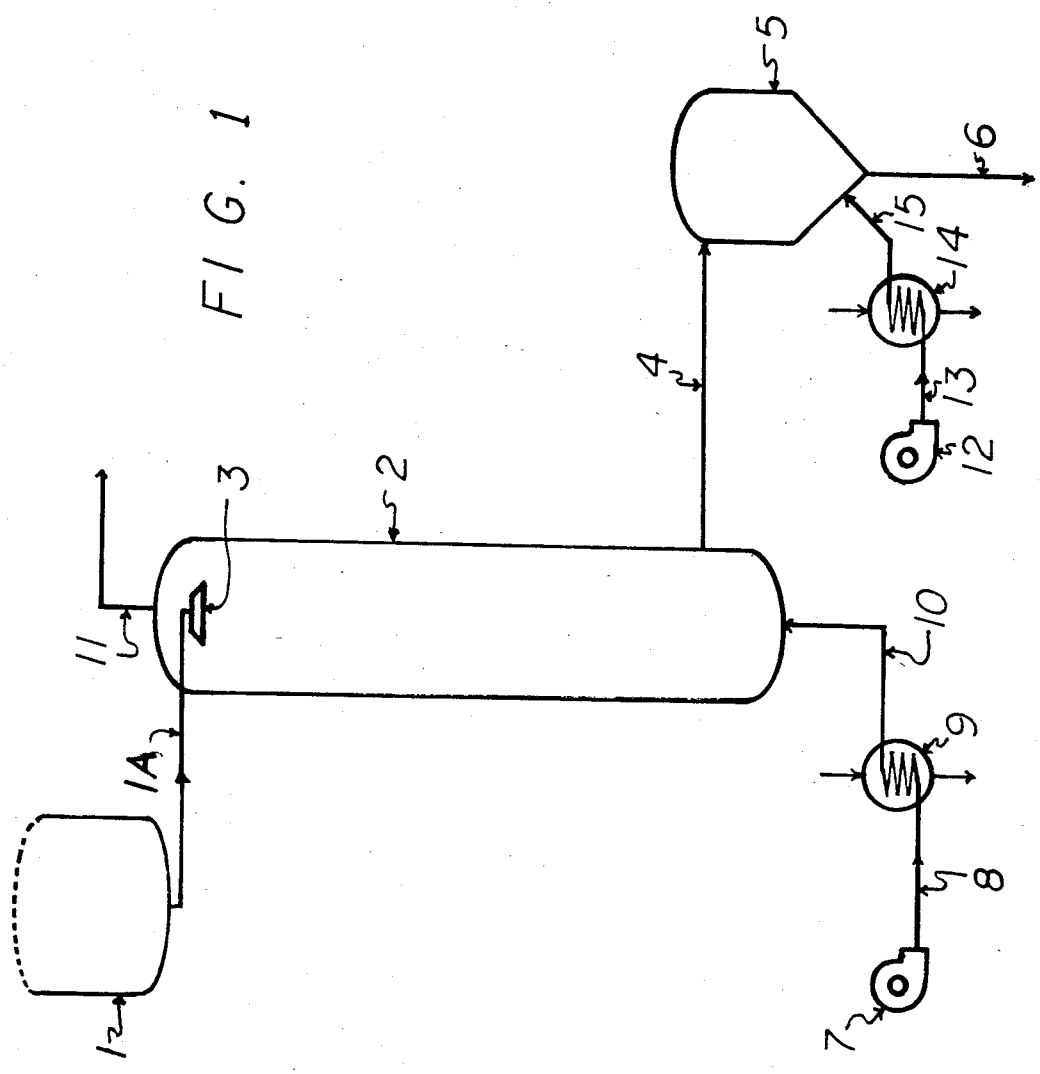

A more detailed description of the present invention is presented by reference to the accompanying drawing, FIG. 1, which is provided for explanative purposes only and is not meant to define or limit the scope of the invention.

An aqueous solution containing at least about 85% by weight of formaldehyde which may or may not have been previously cured, in a manner well-known to the prior art to increase the molecular weight of the organic formaldehyde polymer by formation of methylene glycol units according to the formula:

$$nHCHO + H_2O \rightarrow H(CH_2O)_nOH$$

is admixed with a sufficient source of sodium cation to provide a final sodium Na+ concentration of about 0.5 to about 5 ppm by weight and aged in a holding tank, as for example in tank 1 and tranfer line 1a, for about 10 to about 60 minutes at from about 100° to about 130° C. to speed the polymerization of the formaldehyde after the solution has been fed to the prilling tower 2. The mixture, after aging, is fed through the prilling nozzle 3 into the prilling tower 2. The atmosphere in the prilling tower 2 is gaseous and the flow is countercurrent to the flow of the formaldehyde droplets as they traverse the prilling tower 3. Typically, the atmosphere may be air, nitrogen, or any other material which will not react with the formaldehyde and is in the gas phase at the internal temperature of the tower. By way of example, when air is used as the atmosphere in the prilling tower, fan 7 is used to provide air through line 8 which has been heated to an appropriate temperature in heat exchanger 9 to provide a final temperature in the bottom of the prilling tower 2 of about 45° to about 60° C. The heated air is then led through line 10 to the opposite end of the prilling tower 2 from the nozzle 3 and acts as a countercurrent flow to the droplets of formaldehyde being released from the nozzle. The excess air is removed from the prilling tower through line 11. As the droplets of formaldehyde fall through the counter-current gaseous atmosphere, they solidify into round, solid prills and are collected in a fluidized bed until their temperature is about 45° to about 60° C. The prills are led from the prilling tower by line 4 to a separate aging tank 5. The prills in tank 5 are cooled by a counter current gaseous atmosphere, as for example, air, or nitrogen. They flow in a plugged flow manner and are subject to limited backmixing during their residence time in the tank 5. Typically, fan 12 collects air which is led by line 13 through heat exchanger 14 and then to tank 5 through line 15. Heat exchanger 14 provides air at a temperature sufficient to cool the prills to about 15° to about 30° C. in from about 3 to about 5 hrs. After curing in the aging tank for from about 3 to about 5 hrs, the prills are led through line 6 to storage.

In a preferred embodiment, the temperature of the air entering the prilling tower 2 in line 10 is about 55° C.; the temperature of the air leaving the prilling tower through line 11 is about 75° C., the temperature of the paraformaldehyde prills leaving the tower through line 4 is about 50° C., the temperature of the air entering the aging tank through line 15 is about 18° C., and the temperature of the paraformaldehyde prills passing to storage through line 6 is at about 35° C.

Little or no temperature rise is noted in bulk storage samples of 2000 lbs or more of paraformaldehyde prills manufactured by the improved method of this invention. Further, the prills manufactured by this invention have polymerized to a point where they are reasonably stable as compared to prior art paraformaldehyde prills manufactured by presently available processes. For example, paraformaldehyde prills manufactured by the present invention have a melting point range of from 115° to 120° C. immediately after manufacture and the melting point does not reach 165° C. for up to 300 days bulk storage at room temperature. The prills are soluble in water to provide a clear, non-turbid, colorless solution at all concentrations and temperatures where formaldehyde is normally soluble.

We claim:

1. In process of manufacturing paraformaldehyde prills not subject to autocatalyzed polymerization during storage from an aqueous solution containing at least about 85 weight percent formaldehyde which comprises continuously: (a) polymerizing the formaldehyde in the presence of a basic catalyst; (b) extruding the polymerized formaldehyde through a nozzle to form prills which fall into a countercurrent flow of gas in a tower to further polymerize and solidify the product; (c) collecting the solidified prills; and (d) removing the prills of solid paraformaldehyde from the tower, the improvement which consists of:
    (1) admixing an aqueous solution containing sodium hydroxide with the aqueous formaldehyde to a final sodium ion concentration of from about 0.5 to about 5 parts per million;
    (2) aging the resulting mixture by holding the mixture at from about 100° C. to about 130° C. for about 10 to about 60 minutes to further polymerize the formaldehyde;
    (3) extruding the aged mixture into the tower at from about 100° to about 130° C.;
    (4) removing the prills into a separate quenching vessel wherein the prills further polymerize and dry at from about 15° to about 30° C., for from about 3 to about 5 hours; and
    (5) operating the quenching vessel continuously in a plugged flow manner.

* * * * *